United States Patent
Morgan et al.

(10) Patent No.: US 12,369,840 B2
(45) Date of Patent: Jul. 29, 2025

(54) SYSTEM AND METHOD FOR CARDIAC MAPPING

(71) Applicant: ST. JUDE MEDICAL, CARDIOLOGY DIVISION, INC., St. Paul, MN (US)

(72) Inventors: Dennis J. Morgan, Crystal, MN (US); Don C. Deno, Andover, MN (US); Emma K. Davis, St. Paul, MN (US); Thomas P Hartley, Menomonie, WI (US); Mark Hagfors, North Oaks, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 589 days.

(21) Appl. No.: 17/603,512

(22) PCT Filed: May 22, 2020

(86) PCT No.: PCT/US2020/034222
§ 371 (c)(1),
(2) Date: Oct. 13, 2021

(87) PCT Pub. No.: WO2020/242940
PCT Pub. Date: Dec. 3, 2020

(65) Prior Publication Data
US 2022/0183610 A1  Jun. 16, 2022

Related U.S. Application Data

(60) Provisional application No. 62/852,379, filed on May 24, 2019.

(51) Int. Cl.
*A61B 5/367* (2021.01)
*A61B 5/341* (2021.01)
(Continued)

(52) U.S. Cl.
CPC .............. *A61B 5/367* (2021.01); *A61B 5/341* (2021.01); *A61B 5/35* (2021.01); *A61B 5/287* (2021.01)

(58) Field of Classification Search
CPC ...................................... A61B 5/367
(Continued)

(56) References Cited

U.S. PATENT DOCUMENTS 5,697,377 A  12/1997  Wittkampf
5,983,126 A  11/1999  Wittkampf
(Continued)

FOREIGN PATENT DOCUMENTS

CN  107087290 A  8/2017
EP  2 656 784 A1  10/2013
(Continued)

OTHER PUBLICATIONS

International Preliminary Report on Patentability Chapter I received for International PCT Application Serial No. PCT/US2020/034222 dated Dec. 2, 2021 9 pages.
(Continued)

*Primary Examiner* — Nicole F Johnson
(74) *Attorney, Agent, or Firm* — Wiley Rein LLP (57) ABSTRACT

Electrophysiological activity can be mapped using sub-intervals of electrophsyiological signals. An electroanatomical mapping system receives a plurality of electrophsyiological signals (402), each of which spans an activation interval. For each signal, the system identifies an initial event time within the activation interval, such as by identifying a time of maximum signal energy (404), and defines a sub-interval about the initial event time (406). The system then analyzes the sub-interval to identify one or more electrophysiological characteristics of the electrophysiological signal (408) and adds a corresponding electrophysiology
(Continued)

data point to an electrophysiology map (410). Advantageously, the sub-interval can extend outside of the activation interval, such that the instant teachings allow for capture and analysis of deflections that occur at or near the boundaries of the activation interval.

17 Claims, 7 Drawing Sheets

(51) Int. Cl.
    *A61B 5/35*         (2021.01)
    *A61B 5/287*       (2021.01)

(58) Field of Classification Search
    USPC .......................................................... 600/512
    See application file for complete search history.

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 8,909,502 B2 | 12/2014 | Voth |
| 9,364,160 B2 | 6/2016 | Marziliano et al. |
| 9,474,491 B2 | 10/2016 | Li et al. |
| 10,136,829 B2 | 11/2018 | Deno et al. |
| 10,149,622 B2 | 12/2018 | Narayan et al. |
| 10,296,810 B2 | 5/2019 | Lee et al. |
| 10,441,187 B2 | 10/2019 | Afonso et al. |
| 10,758,147 B2 | 9/2020 | Relan et al. |
| 11,058,342 B2 | 7/2021 | Botzer et al. |
| 11,179,112 B2 | 11/2021 | Li et al. |
| 11,950,917 B2 | 4/2024 | Hagfors et al. |
| 2009/0275827 A1* | 11/2009 | Aiken ..................... A61B 5/06 600/424 |
| 2010/0069921 A1* | 3/2010 | Miller ................ A61B 18/1233 600/301 |
| 2010/0162786 A1 | 7/2010 | Keenan et al. |
| 2011/0166618 A1 | 7/2011 | Zhang et al. |
| 2013/0345577 A1 | 12/2013 | Thakur et al. |
| 2015/0051452 A1* | 2/2015 | Ciaccio .................. G06F 17/14 600/407 |
| 2015/0057507 A1 | 2/2015 | Koyrakh et al. |
| 2015/0196215 A1 | 7/2015 | Laughner et al. |
| 2017/0156612 A1 | 6/2017 | Relan et al. |
| 2017/0202516 A1 | 7/2017 | Bar-Tal et al. |
| 2017/0360319 A1 | 12/2017 | Hagfors et al. |
| 2018/0296111 A1 | 10/2018 | Deno et al. |
| 2020/0253496 A1 | 8/2020 | Deno et al. |

FOREIGN PATENT DOCUMENTS

| | | | |
|---|---|---|---|
| WO | 2016/033075 A1 | 3/2016 | |
| WO | 2017/192301 A1 | 11/2017 | |
| WO | WO-2017192294 A1 * | 11/2017 | ......... A61B 5/04012 |

OTHER PUBLICATIONS

Haldar, Shouvik K. et al.; "Resolving Bipolar Electrogram Voltages During Atrial Fibrillation Using Omnipolar Mapping"; Circulation: Arrhythmia and Electrophysiology, vol. 10, No. 9, Sep. 2017.

Alcaine, et al., "Spatiotemporal Model-Based Estimation of High-Density Atrial Fibrillation Activation Maps", Digital Signal Processing, vol. 54, 2016, pp. 64-74.

Cantwell, et al., "Techniques for Automated Local Activation Time Annotation and Conduction Velocity Estimation in Cardiac Mapping", Computers in Biology and Medicine, 2015, pp. 1-14.

Nakasuka, et al., ""Window Sliding" Analysis Combined with High-Density and Rapid Electroanatomical Mapping: its Efficacy and the Outcome of Catheter Ablation of Atrial Tachycardia", Heart Vessels, Mar. 8, 2017, 13 pages.

Oduneye, et al., "The Feasibility of Endocardial Propagation Mapping Using Magnetic Resonance Guidance in a Swine Model, and Comparison With Standard Electroanatomic Mapping", IEEE Transactions on Medical Imaging, vol. 31, No. 4, Apr. 2012, pp. 977-983.

* cited by examiner

SYSTEM AND METHOD FOR CARDIAC MAPPING

CROSS-REFERENCE TO RELATED APPLICATIONS

This application claims the benefit of U.S. provisional application No. 62/852,379, filed 24 May 2019, which is hereby incorporated by reference as though fully set forth herein.

BACKGROUND

The present disclosure relates generally to cardiac mapping, such as may be performed in cardiac diagnostic and therapeutic procedures. In particular, the present disclosure relates to systems, apparatuses, and methods for generating cardiac geometry and/or electrophysiology maps from data collected by a roving electrophysiology probe, such as a high density ("HD") grid catheter or other multi-electrode device.

Cardiac mapping, including the generation of cardiac geometries and electrocardiographic mapping, is a part of numerous cardiac diagnostic and therapeutic procedures. As the complexity of such procedures increases, however, the geometries and electrophysiology maps utilized must increase in quality, in density, and in the rapidity and ease with which they can be generated.

Electrocardiographic mapping often involves analyzing intracardiac electrograms over a specified time interval (referred to in the art as a "roving activation interval" or "RAI"). Electrogram analysis may be complicated, however, by the presence of multiple deflections within the RAI.

BRIEF SUMMARY

Disclosed herein is a method of mapping electrophysiological activity. The method includes receiving, at an electroanatomical mapping system, a plurality of electrophysiological signals, wherein each electrophysiological signal spans an activation interval. For each electrophysiological signal of the plurality of electrophysiological signals, the electroanatomical mapping system: identifies an initial event time within the activation interval of the electrophysiological signal; defines a sub-interval about the initial event time; analyzes the sub-interval to identify one or more electrophysiological characteristics of the electrophysiological signal; and adds an electrophysiology data point to an electrophysiology map, wherein the electrophysiology data point includes the one or more electrophysiological characteristics of the electrophysiological signal associated with a location at which the electrophysiological signal was measured. The electroanatomical mapping system can also output a graphical representation of the electrophysiology map on an anatomical model.

In aspects of the disclosure, the step of identifying an initial event time within the activation interval of the electrophysiological signal includes using an energy function to identify the initial event time, such as by identifying a time of greatest signal energy of the energy function as the initial event time.

In other aspects of the disclosure, the step of identifying an initial event time within the activation interval of the electrophysiological signal includes using template matching to identify the initial event time, such as by identifying a time of maximum morphological correlation between the electrophysiological signal and a template signal as the initial event time.

In still further aspects of the disclosure, the step of identifying an initial event time within the activation interval of the electrophysiological signal includes using a weighted window function to identify the initial event time.

The teachings herein can be applied to omnipolar electrophysiological signals, such as an omnipolar electrogram defined by at least two bipolar electrograms. The step of identifying an initial event time within the activation interval of the electrophysiological signal can include computing root mean squares of derivatives of the at least two bipolar electrograms to identify the initial event time. Alternatively, the step of identifying an initial event time within the activation interval of the electrophysiological signal can include computing a mean absolute value transform of derivatives of the at least two bipolar electrograms to identify the initial event time.

In some embodiments, the omnipolar electrogram is defined by two (or more) orthogonal bipolar electrograms, and the step of identifying an initial event time within the activation interval of the electrophysiological signal includes computing a norm of derivatives of the two (or more) orthogonal bipolar electrograms to identify the initial event time. The step of identifying the initial event time within the activation interval of the electrophysiological signal can also include at least one of: high-pass filtering the derivatives of the orthogonal bipolar electrograms prior to computing the norm of the derivatives of the two orthogonal bipolar electrograms; and low-pass filtering the computed norm of the derivatives of the two orthogonal bipolar electrograms.

It is contemplated that the step of defining a sub-interval about the initial event time can include defining the sub-interval as an interval of preset duration centered on the initial event time. It is also contemplated that the step of defining a sub-interval about the initial event time can include: the electroanatomical mapping system receiving user input defining a duration of the sub-interval; and defining the sub-interval as an interval of the user-defined duration centered on the initial event time.

In embodiments of the disclosure, the sub-interval extends outside of the activation interval (e.g., the roving activation interval, or RAI).

Also disclosed herein is a method of mapping electrophysiological activity, including: receiving, at an electroanatomical mapping system, a plurality of electrophysiological signals; and for each electrophysiological signal of the plurality of electrophysiological signals, the electroanatomical mapping system: processing the electrophysiological signal to define a sub-interval including a deflection of interest; analyzing only the sub-interval to identify one or more electrophysiological characteristics of the electrophysiological signal; and adding an electrophysiology data point to an electrophysiology map, wherein the electrophysiology data point includes the one or more electrophysiological characteristics of the electrophysiological signal associated with a location at which the electrophysiological signal was measured.

The electrophysiological signal can include an omnipolar electrogram defined by at least two bipolar electrograms; in some embodiments, the at least two bipolar electrograms include a pair of orthogonal bipolar electrograms.

The method optionally includes the electroanatomical mapping system outputting a graphical representation of the electrophysiology map on an anatomical model.

According to aspects of the disclosure, the sub-interval is centered on the deflection of interest.

The instant disclosure also provides an electroanatomical mapping system, including a sub-interval definition processor configured to: receive an electrophysiological signal spanning an activation interval; identify, within the activation interval of the electrophysiological signal, a deflection of interest; and define a sub-interval about the deflection of interest. The electroanatomical mapping system further includes a mapping processor configured to: analyze the sub-interval to identify (e.g., quantify) one or more electrophysiological characteristics of the electrophysiological signal; and add an electrophysiology data point to an electrophysiology map, wherein the electrophysiology data point includes the one or more electrophysiological characteristics of the electrophysiological signal associated with a location at which the electrophysiological signal was measured.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating electrophysiology maps. For purposes of illustration, aspects of the disclosure will be described with reference to cardiac electrophysiology procedures. More specifically, aspects of the disclosure will be described in the context of the creation of cardiac electrophysiology maps from intracardiac electrograms collected using a high density (HD) grid catheter, such as the Advisor™ HD grid mapping catheter from Abbott Laboratories (Abbott Park, Illinois), in conjunction with an electroanatomical mapping system, such as the EnSite Precision™ cardiac mapping system, also from Abbott Laboratories.

Those of ordinary skill in the art will understand, however, how to apply the teachings herein to good advantage in other contexts and/or with respect to other devices. For instance, the instant teachings can likewise be applied to other electrophysiological signals, such as unipolar and/or bipolar electrograms received from other electrophysiology catheters, including, without limitation, the Flexibility™, Advisor™, Reflexion™, Inquiry™, and/or Livewire™ electrophysiology catheters, all from Abbott Laboratories.

Figure 1:
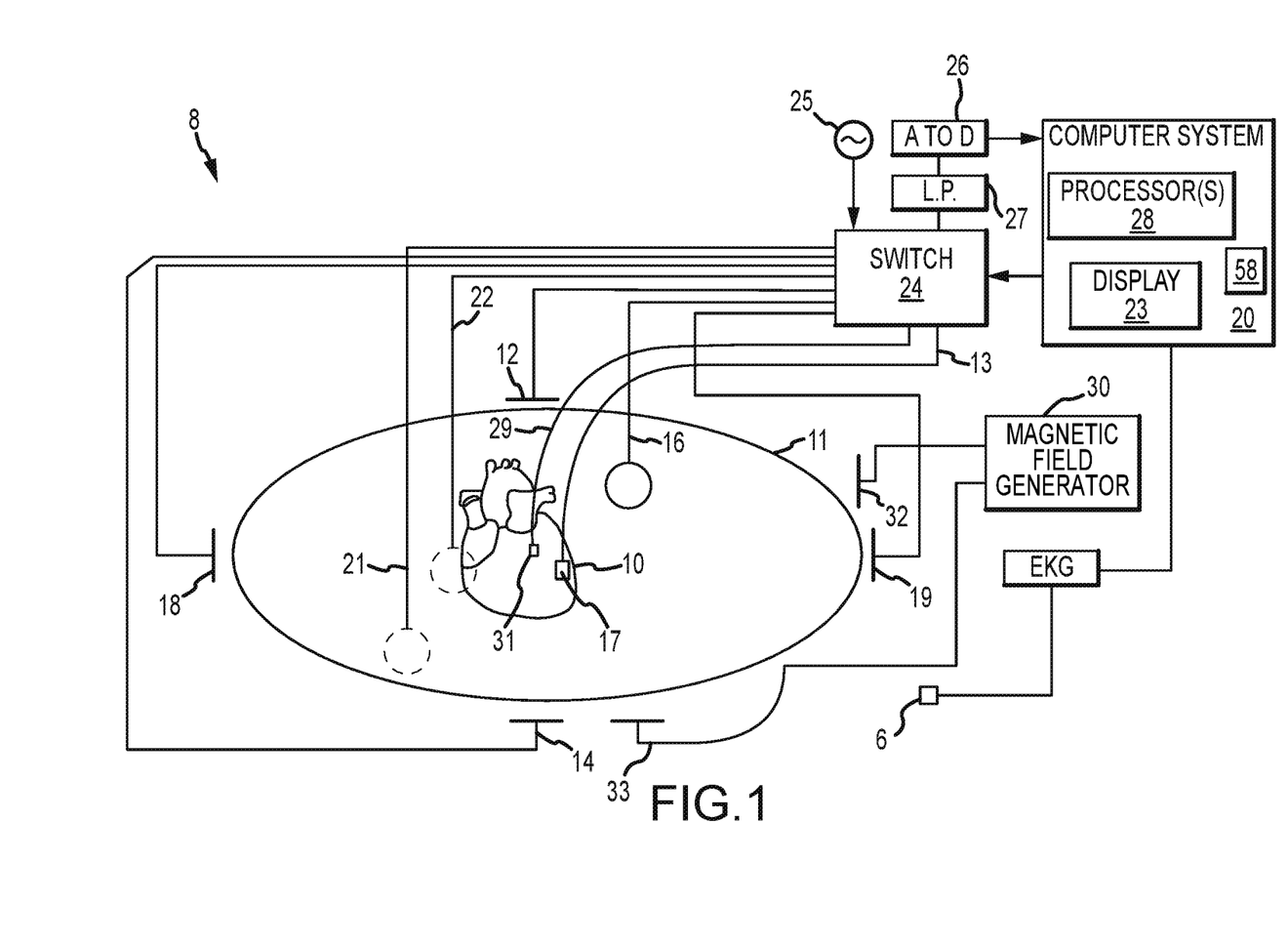
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
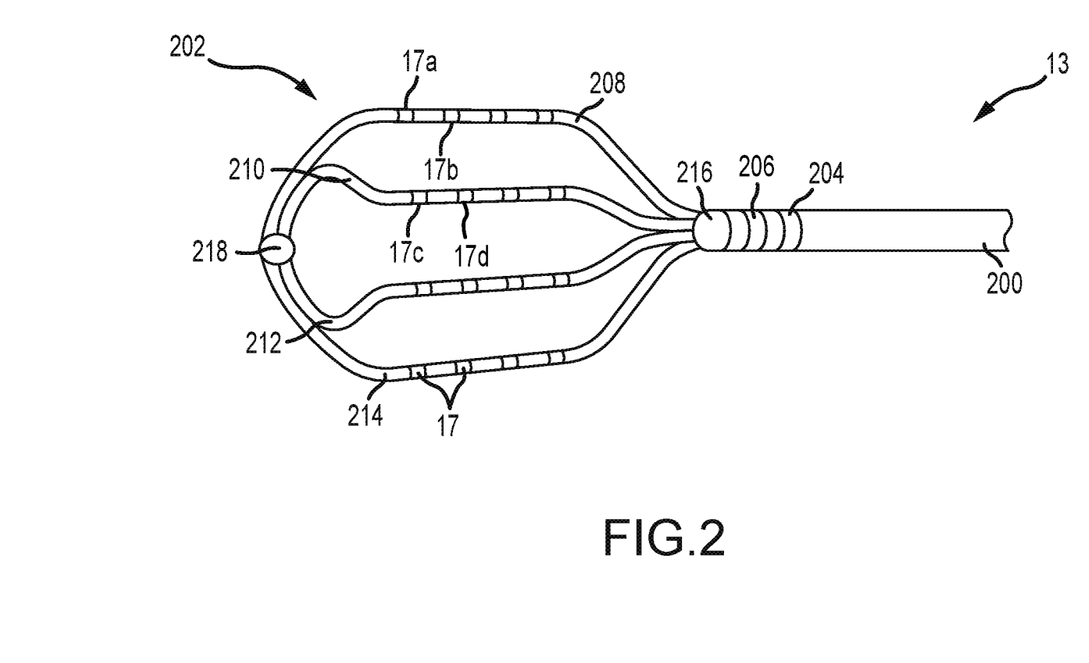
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

Figure 3A:
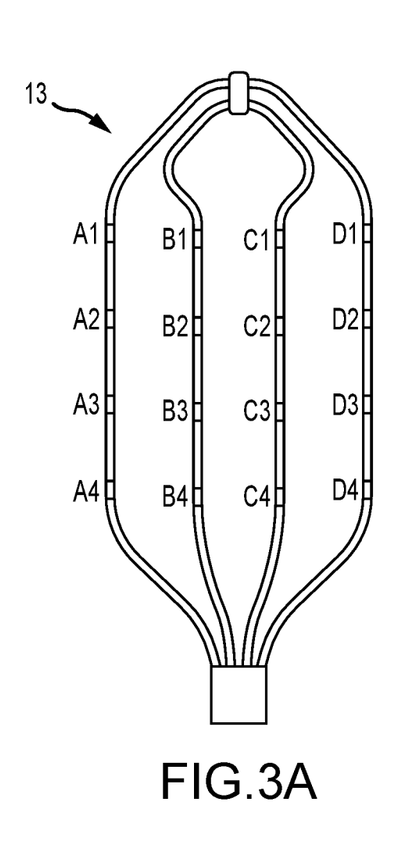
FIGS. 3A and 3B provide alphanumeric labeling conventions for electrodes carried by a multi-electrode catheter and the bipoles associated therewith.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214. For purposes of easy reference in this description, FIG. 3A provides alphanumeric labels for electrodes 17.

As those of ordinary skill in the art will recognize, any two neighboring electrodes 17 define a bipole. Thus, the 16 electrodes 17 on catheter 13 define a total of 42 bipoles—12 along splines (e.g., between electrodes 17a and 17b, or between electrodes 17c and 17d), 12 across splines (e.g., between electrodes 17a and 17c, or between electrodes 17b and 17d), and 18 diagonally between splines (e.g., between electrodes 17a and 17d, or between electrodes 17b and 17c).

Figure 3B:
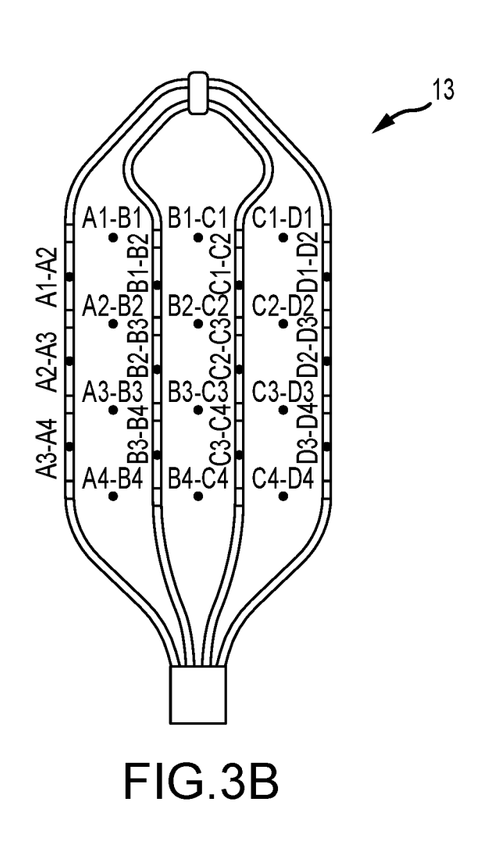

For ease of reference in this description, FIG. 3B provides alphanumeric labels for the along- and across-spline bipoles. FIG. 3B omits alphanumeric labels for the diagonal bipoles, but this is only for the sake of clarity in the illustration. It is expressly contemplated that the teachings herein can also be applied with respect to the diagonal bipoles.

Any bipole can, in turn, be used to generate a bipolar electrogram according to techniques that will be familiar to those of ordinary skill in the art. Moreover, these bipolar electrograms can be combined (e.g., linearly combined) to generate electrograms, again including activation timing information, in any direction of the plane of catheter 13 by computing an E-field or voltage loop for a clique of electrodes. United States patent application publication no. 2018/0296111 (the '111 publication), which is hereby incorporated by reference as though fully set forth herein, discloses details of computing an E-field loop for a clique of electrodes on a HD grid catheter.

In any event, catheter 13 can be used to simultaneously collect a plurality of electrophysiology data points for the various bipoles defined by electrodes 17 thereon, with each such electrophysiology data point including both localization information (e.g., position and orientation of a selected bipole) and an electrogram signal for the selected bipole. For purposes of illustration, methods according to the instant disclosure will be described with reference to individual electrophysiology data points collected by catheter 13. It should be understood, however, that the teachings herein can be applied, in serial and/or in parallel, to multiple electrophysiology data points collected by catheter 13.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario), Sterotaxis, Inc.'s NIOBE® Magnetic Navigation System (St. Louis, Missouri), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to generating electrophysiology maps, and in particular to generating electrophysiology maps using sub-intervals of electrophysiological signals. Graphical representations of such electrophysiology maps can also be output, for example on display 23. System 8 can therefore include a sub-interval definition module 58, which may further include a mapping module to generate an electrophysiology map and, optionally, output a graphical representation of the same (e.g., to display 23).

Figure 4:
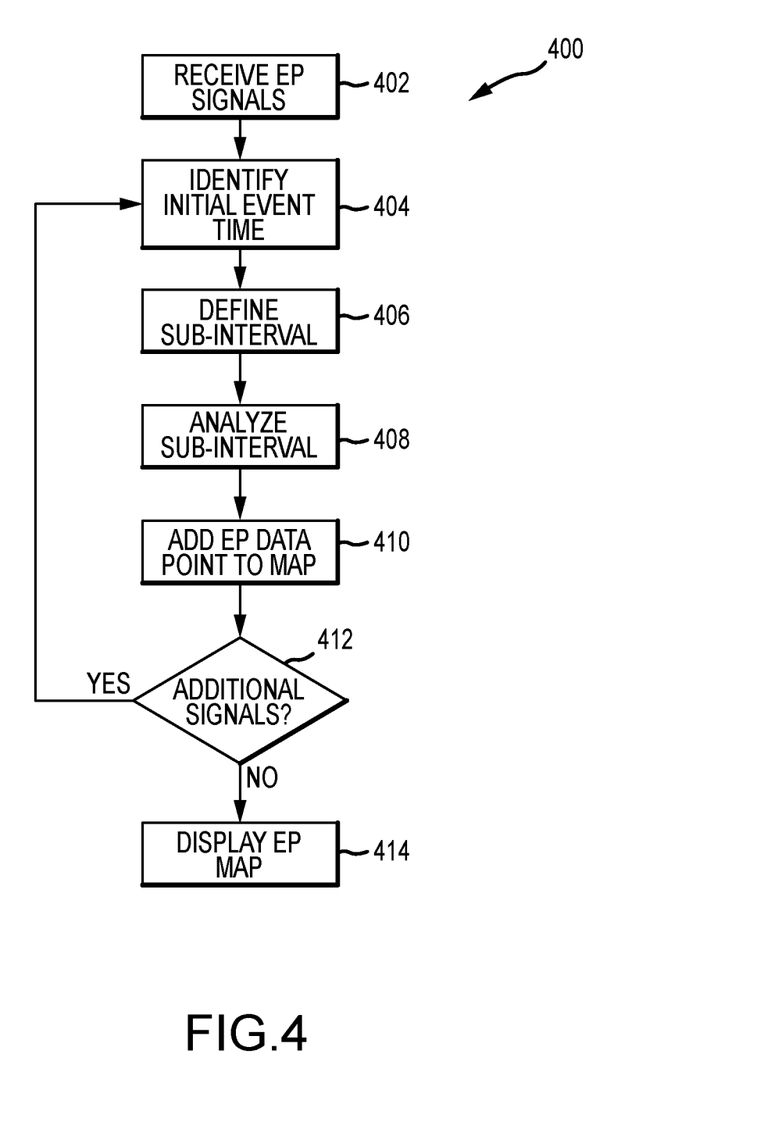
FIG. 4 is a flowchart of representative steps that can be carried out according to exemplary embodiments disclosed herein.

An exemplary method of mapping electrophysiological activity will be explained with reference to the flowchart 400 of representative steps presented as FIG. 4. In some embodiments, for example, flowchart 400 may represent several exemplary steps that can be carried out by electroanatomical mapping system 8 of FIG. 1 (e.g., by processor 28 and/or sub-interval definition module 58). It should be understood that the representative steps described below can be either hardware- or software-implemented. For the sake of explanation, the term "signal processor" is used herein to describe both hardware- and software-based implementations of the teachings herein.

Figure 5:
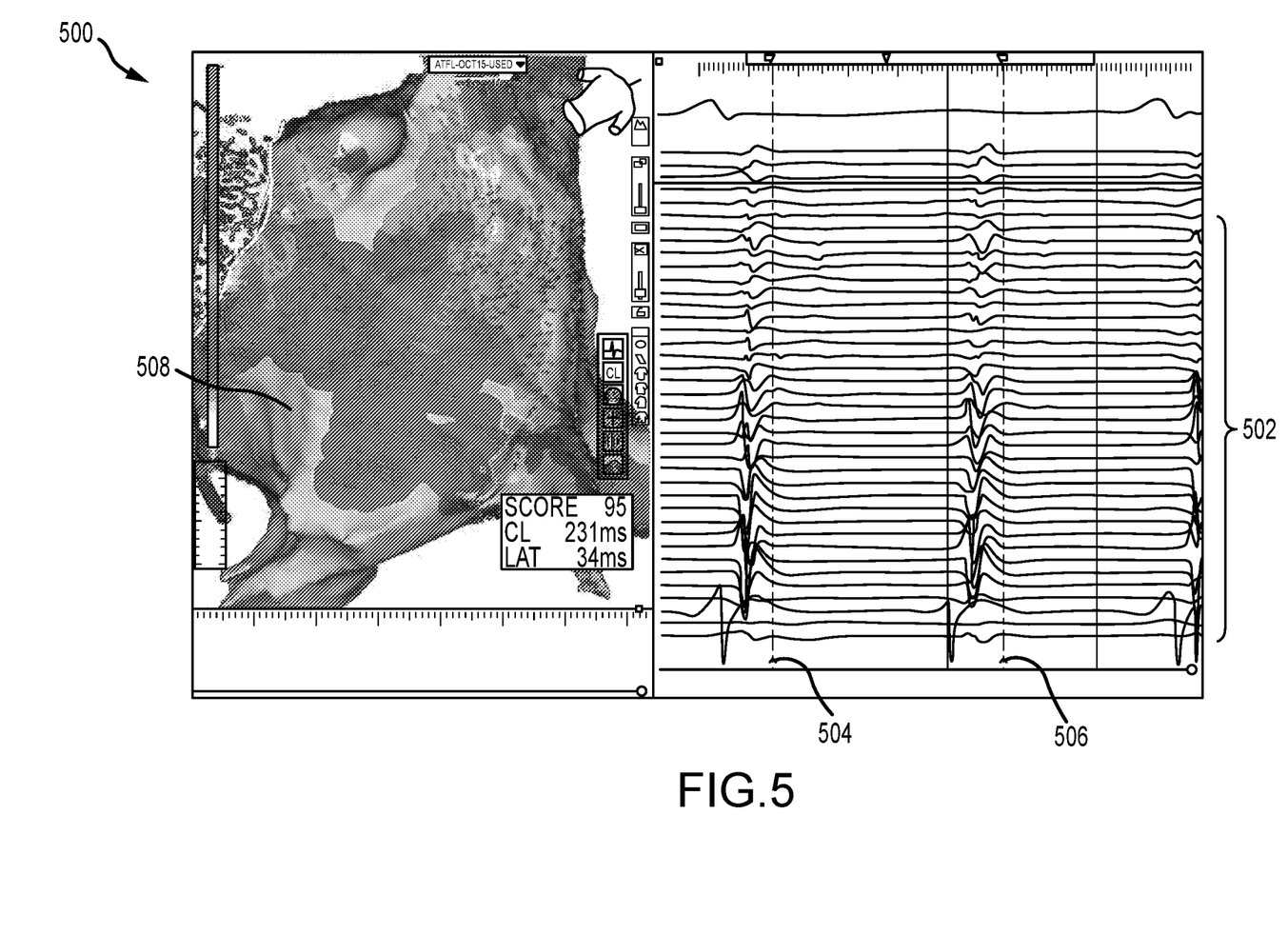
FIG. 5 is an illustrative screen from an electroanatomical mapping system depicting a graphical representation of an electrophysiology map side-by-side with omnipolar electrogram traces.

In block 402, system 8 receives a plurality of electrophysiological signals. For purposes of illustration, aspects of the disclosure will be described with reference to omnipolar electrograms. In this regard, FIG. 5 depicts a representative output 500 of system 8 to display 23, including a plurality of traces 502. Each trace depicts an omnipolar electrogram for a clique of three electrodes 17 on HD grid catheter 13, as computed, for example, according to the teachings of the '111 publication. The RAI for each electrophysiological signal is the unshadowed region between carats 504, 506.

In block 404, system 8 identifies a deflection of interest within the activation interval of a given electrophysiological signal. The term "initial event time" is used herein to refer to the timing of the deflection of interest so identified In aspects of the disclosure, system 8 uses an energy function of the given electrophysiological signal to identify the initial event time. For instance, the initial event time can be identified as the time at which the energy function of the electrophysiological signal has the greatest signal energy, such as may be determined through wavelet domain transformation and analysis of the given electrophysiological signal. Additional approaches to identifying the time of maximum signal energy are described below.

In other aspects of the disclosure, system 8 uses template matching to identify the initial event time. For instance, the initial event time can be identified as the time of maximum morphological correlation between the given electrophysiological signal and a template signal that exhibits the deflection of interest. By way of illustration only, United States patent application publication no. 2015/0057507, which is hereby incorporated by reference as though fully set forth herein, describes exemplary approaches to computing morphological similarities between electrophysiological signals.

In still other aspects of the disclosure, system 8 uses a weighted window function to identify the initial event time. For example, it may be desirable to characterize late potentials during certain electrophysiology studies (e.g., when mapping regular reentrant arrhythmias, a practitioner may be particularly interested in deflections that happen after most of the chamber has activated). In such studies, a voltage weighting function that increases with time can be applied to the given electrophysiological signal within the RAI in order to facilitate identification of the late deflection of interest.

Those of ordinary skill in the art will also appreciate from the foregoing discussion that a weighted window function could also be employed to identify early potentials. Thus, it is contemplated that the window function may be time aligned to the edges of the RAI (e.g., to carat 504 or 506 in FIG. 5, depending on whether early or late potentials are of interest), to surface electrocardiogram deflections, and/or to specific intracardiac electrogram features.

The '111 publication describes another suitable approach to initial event time identification in omnipolar electrograms by identifying the time of maximum energy of the omnipolar electrogram within the RAI. Because the deflection of interest is often characterized by a high slew rate, a high amplitude, and high frequency components within the given electrophysiological signal, the '111 publication describes differentiating the two or more bipolar electrograms that define the omnipolar electrogram.

According to some aspects of the disclosure, the time of maximum energy can be identified by computing root mean squares of the derivatives of the bipolar electrograms that define the omnipolar electrogram. In alternative aspects of the disclosure, the time of maximum energy can be identified by computing root mean squares or simple square means of the bipolar electrograms that define the omnipolar electrogram.

According to other aspects of the disclosure, the time of maximum energy can be identified by computing an absolute value transform of the derivatives of the bipolar electrograms that define the omnipolar electrogram.

In still other aspects of the disclosure, and in particular where the omnipolar electrogram is defined by an orthogonal pair of bipolar electrograms (as may be the case with an HD grid catheter as shown in FIG. 2), the time of maximum energy can be identified by computing a norm of the derivatives of the bipolar electrograms. To further emphasize the desired deflection in the omnipolar electrogram, the derivatives of the bipolar electrograms may be high-pass filtered prior to computing their norm and/or the computed norm may be low-pass filtered.

Figure 6:
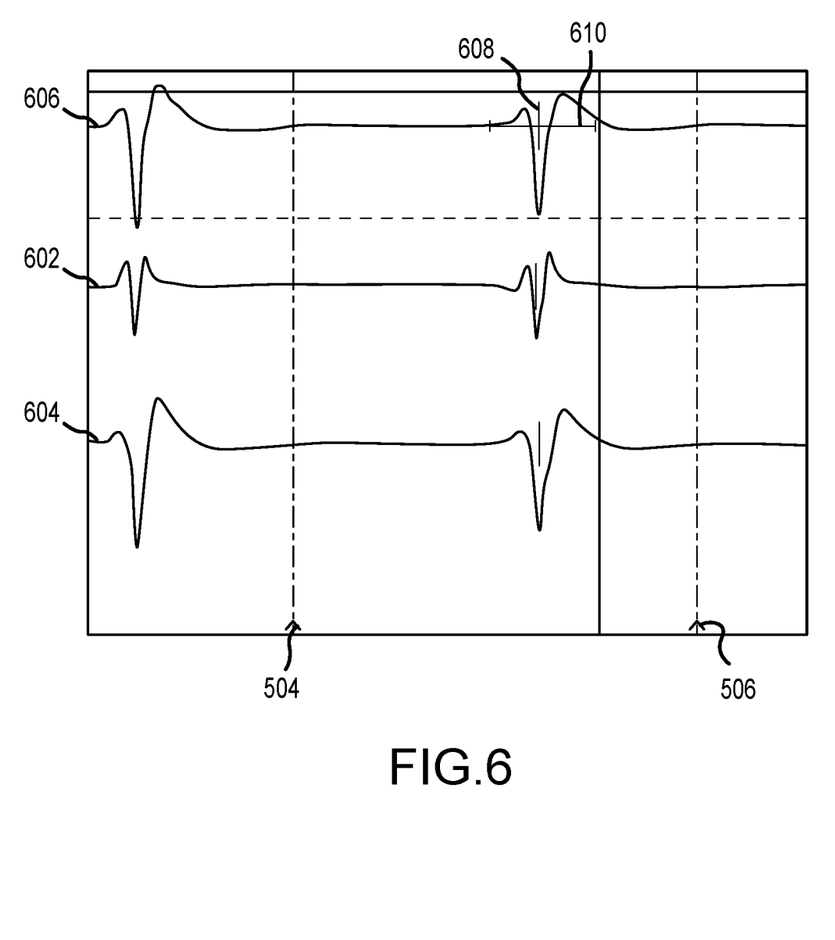
FIG. 6 is a close-up view of an omnipolar electrogram and its constituent bipolar electrograms, marked to show initial event times and sub-intervals according to aspects of the present disclosure.

FIG. 6 depicts the identification of the initial event time in an omnipolar electrogram for a clique of electrodes A1, B1, and B2 (see FIG. 3A). In the lower portion of FIG. 6 are two bipolar electrograms 602, 604 corresponding to bipoles B1-B2 and A1-B1, respectively (see FIG. 3B). The top portion of FIG. 6 shows the corresponding omnipolar electrogram 606 for the three-electrode clique. By computing the norm of the derivatives of bipolar electrograms 602, 604 (optionally including high- and/or low-pass filtering as described above), system 8 can generate an energy function for omnipolar electrogram 606 and identify therefrom the time of maximum signal energy and designate that time as the initial event time, represented in FIG. 6 by tick mark 608.

As described above, an orientation-independent energy function is generated for an orientation-independent omnipolar electrogram (e.g., 606), which is in turn defined by two or more bipolar electrograms (e.g., orthogonal bipolar electrograms 602, 604). It is also within the instant teachings, however, to generate energy functions for the underlying bipolar electrograms, which energy functions can, in turn, be composed into an orientation-independent energy function.

Returning now to FIG. 4, once the initial event time is identified, system 8 next defines a sub-interval about the initial event time in block 406. In embodiments of the disclosure, the sub-interval is centered on the initial event time, as shown by 60 ms wide caliper mark 610 in FIG. 6. It should be understood, however, that the sub-interval need not be centered on the initial event time; indeed, a practitioner may wish to adjust how much of the sub-interval occurs before the initial event time and how much of the sub-interval occurs after the initial event time.

The sub-interval may have a preset width (that is, a preset duration). Alternatively, system 8 may permit a practitioner to adjust the width of the sub-interval (e.g., by presenting, via a graphical user interface on display 23, a control that permits the user to vary the width of the sub-interval).

It should also be understood that, although aspects of the disclosure constrain the initial event time to within the RAI, the sub-interval need not be so constrained, and can extend outside of the RAI. Allowing the sub-interval to extend outside of the RAI can facilitate identification of morphologies that might otherwise be excluded because they occur too close to the boundaries of the RAI.

For instance, when mapping a regular reentrant arrhythmia, the RAI may generally be set close to the cycle length. Yet, physiologic but regular tachycardias may have cycle lengths that vary by between about 5 ms and about 10 ms. By definition in a reentrant arrhythmia, there is always some part of the cardiac tissue that is depolarizing, with individual depolarization events lasting between about 7 ms and about 70 ms. Some of these events may occur near the edges of the RAI. Depending on cycle length variability, therefore, the RAI may include no depolarization events, one complete depolarization event, one partial depolarization event, or two partial depolarization events. In such circumstances, the instant teachings can be applied to good advantage to identify, and then analyze, a depolarization event that is not fully within the RAI.

Figure 7:
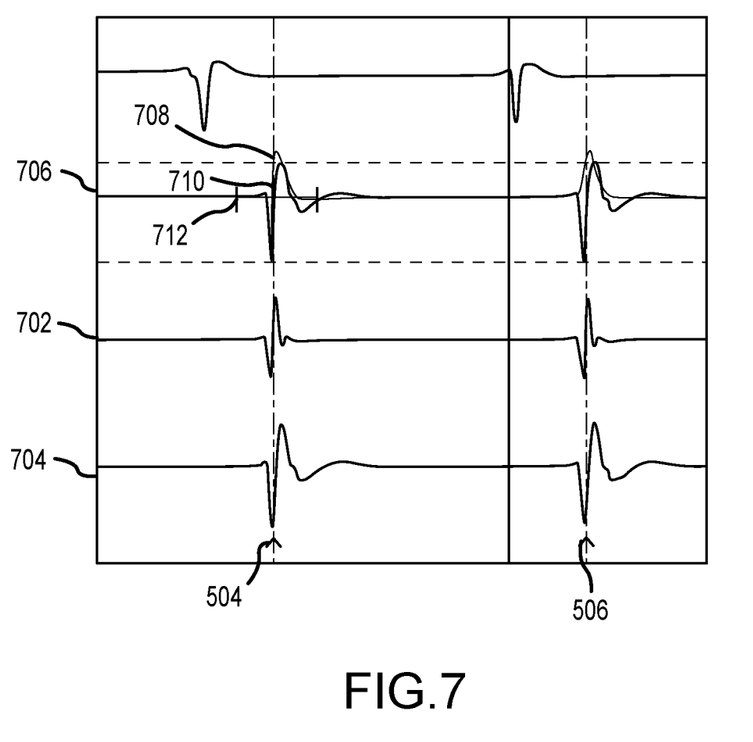
FIG. 7 is a close-up view of an omnipolar electrogram, an energy function for the same, and its constituent bipolar electrograms, marked to show initial event times and sub-intervals according to aspects of the present disclosure.

For instance, FIG. 7 illustrates the identification of an initial event time in the case of atrial flutter. Bipolar electrograms 702, 704, respectively corresponding to bipoles C1-C2 and B1-C1 on catheter 13, exhibit two deflections within the RAI (e.g., between carats 504, 506). Omnipolar electrogram 706 for electrode clique C1-C2-B1 likewise has two deflections within the RAI. Energy function 708, however, has its maximum energy at the earlier of the two deflections, and thus system 8 designates the earlier deflection as the initial event time 710. The resultant sub-interval 712 extends prior to the start of the RAI (e.g., earlier than carat 504).

In block 408, system 8 analyzes the sub-interval to identify one or more electrophysiological characteristics of the given electrophysiological signal. For instance, rather than analyzing the entirety of omnipolar electrogram 606 or 706 to determine peak-to-peak voltage, local activation times, and the like, system 8 instead limits its analysis to sub-interval 610 or 710 to identify these same characteristics. If desired, bipolar electrograms (e.g., 702, 704) can also be analyzed over the same sub-interval. A corresponding electrophysiology data point can be added to an electrophysiology map in block 410.

Decision block 412 initiates a loop back to block 404 in order to process additional electrophysiological signals received in block 402. Once all signals have been processed, decision block 412 follows the "NO" exit to block 414, where system 8 can output a graphical representation of the electrophysiology map on an anatomical model (e.g., model 508 in FIG. 5, as output on display 23).

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, it is contemplated that the width of the sub-interval can be computationally determined by system 8, such as based on voltage or E-field loop deviations from isoelectric points.

As yet another example, a single sub-interval duration may be used for all electrode cliques within a preset neighborhood distance. For instance, the sub-interval duration can be set for the centrally located, four-electrode clique B2-C2-C3-B3, and this same sub-interval duration can be used for all three-electrode cliques on catheter 13.

As a still further example, the teachings of United States patent application publication no. 2017/0156612, which is hereby incorporated by reference as though fully set forth herein, can be applied to good advantage in conjunction with the instant teachings (in particular, to initial event time identification in block 404).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping electrophysiological activity, comprising:
   receiving from an electrophysiology catheter, at an electroanatomical mapping system including a display and a plurality of localization field generators that generate a non-ionizing localization field to measure a location of the electrophysiology catheter within the non-ionizing localization field, a plurality of electrophysiological signals measured by the electrophysiology catheter, wherein each electrophysiological signal spans an activation interval, and wherein each electrophysiological signal of the plurality of electrophysiological signals comprises an omnipolar signal; and
   for each electrophysiological signal of the plurality of electrophysiological signals, the electroanatomical mapping system:
      identifying an initial event time within the activation interval of the electrophysiological signal;
      defining a sub-interval about the initial event time;
      analyzing the sub-interval to identify one or more electrophysiological characteristics of the electrophysiological signal; and
      adding an electrophysiology data point to an electrophysiology map, wherein the electrophysiology data point includes the one or more electrophysiological characteristics of the electrophysiological signal associated with the location of the electrophysiology catheter at which the electrophysiological signal was measured; and
   outputting on the display a graphical representation of the electrophysiology map on an anatomical model.

2. The method according to claim 1, wherein identifying an initial event time within the activation interval of the electrophysiological signal comprises using an energy function to identify the initial event time.

3. The method according to claim 2, wherein using an energy function to identify the initial event time comprises identifying a time of greatest signal energy of the energy function as the initial event time.

4. The method according to claim 1, wherein identifying an initial event time within the activation interval of the electrophysiological signal comprises using template matching to identify the initial event time.

5. The method according to claim 4, wherein using template matching to identify the initial event time comprises identifying a time of maximum morphological correlation between the electrophysiological signal and a template signal as the initial event time.

6. The method according to claim 1, wherein identifying an initial event time within the activation interval of the electrophysiological signal comprises using a weighted window function to identify the initial event time.

7. The method according to claim 1, wherein the omnipolar signal comprises an omnipolar electrogram defined by at least two bipolar electrograms, and wherein identifying an initial event time within the activation interval of the electrophysiological signal comprises computing root mean squares of derivatives of the at least two bipolar electrograms to identify the initial event time.

8. The method according to claim 1, wherein the omnipolar signal comprises an omnipolar electrogram defined by at least two bipolar electrograms, and wherein identifying an initial event time within the activation interval of the electrophysiological signal comprises computing a mean absolute value transform of derivatives of the at least two bipolar electrograms to identify the initial event time.

9. The method according to claim 1, wherein the omnipolar signal comprises an omnipolar electrogram defined by two orthogonal bipolar electrograms, and wherein identifying an initial event time within the activation interval of the electrophysiological signal comprises computing a norm of derivatives of the two orthogonal bipolar electrograms to identify the initial event time.

10. The method according to claim 9, wherein identifying the initial event time within the activation interval of the electrophysiological signal further comprises at least one of:
high-pass filtering the derivatives of the orthogonal bipolar electrograms prior to computing the norm of the derivatives of the two orthogonal bipolar electrograms; and
low-pass filtering the computed norm of the derivatives of the two orthogonal bipolar electrograms.

11. The method according to claim 1, wherein defining a sub-interval about the initial event time comprises defining the sub-interval as an interval of preset duration centered on the initial event time.

12. The method according to claim 1, wherein defining a sub-interval about the initial event time comprises:
the electroanatomical mapping system receiving user input defining a duration of the sub-interval; and
defining the sub-interval as an interval of the user-defined duration centered on the initial event time.

13. The method according to claim 1, wherein the sub-interval extends outside of the activation interval.

14. A method of mapping electrophysiological activity, comprising:
receiving from an electrophysiology catheter, at an electroanatomical mapping system including a display and a plurality of localization field generators that generate a non-ionizing localization field to measure a location of the electrophysiology catheter within the non-ionizing localization field, a plurality of electrophysiological signals measured by the electrophysiology catheter, wherein each electrophysiological signal of the plurality of electrophysiological signals comprises an omnipolar electrogram defined by at least two bipolar electrograms; and for each electrophysiological signal of the plurality of electrophysiological signals, the electroanatomical mapping system:
processing the electrophysiological signal to define a sub-interval including a deflection of interest;
analyzing only the sub-interval to identify one or more electrophysiological characteristics of the electrophysiological signal; and
adding an electrophysiology data point to an electrophysiology map, wherein the electrophysiology data point includes the one or more electrophysiological characteristics of the electrophysiological signal associated with the location of the electrophysiology catheter at which the electrophysiological signal was measured; and
outputting on the display a graphical representation of the electrophysiology map on an anatomical model.

15. The method according to claim 14, wherein the at least two bipolar electrograms comprises a pair of orthogonal bipolar electrograms.

16. The method according to claim 14, wherein the sub-interval is centered on the deflection of interest.

17. An electroanatomical mapping system, comprising:
a plurality of localization field generators that generate a non-ionizing localization field to measure a location of an electrophysiology catheter within the non-ionizing localization field;
a display; and
a sub-interval definition processor configured to:
receive from the electrophysiology catheter within the non-ionizing localization field an omnipolar electrophysiological signal spanning an activation interval;
identify, within the activation interval of the electrophysiological signal, a deflection of interest; and
define a sub-interval about the deflection of interest; and
a mapping processor configured to:
analyze the sub-interval to identify one or more electrophysiological characteristics of the electrophysiological signal;
add an electrophysiology data point to an electrophysiology map, wherein the electrophysiology data point includes the one or more electrophysiological characteristics of the electrophysiological signal associated with a location at which the electrophysiological signal was measured; and
output on the display a graphical representation of the electrophysiology map on an anatomical model.

* * * * *